United States Patent
Bang et al.

(10) Patent No.: US 10,406,180 B2
(45) Date of Patent: Sep. 10, 2019

(54) COMPOSITION INCLUDING STEM CELL-DERIVED MICROVESICLES FOR PROMOTING NEUROGENESIS

(71) Applicant: SAMSUNG LIFE PUBLIC WELFARE FOUNDATION, Seoul (KR)

(72) Inventors: Oh Young Bang, Seoul (KR); Gyeong Joon Moon, Seongnam-si (KR); Yeon Hee Cho, Seoul (KR); Suk Jae Kim, Seoul (KR); Dong Hee Kim, Seoul (KR); Ji Hee Sung, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 15/649,842

(22) Filed: Jul. 14, 2017

(65) Prior Publication Data

US 2017/0368103 A1    Dec. 28, 2017

Related U.S. Application Data

(62) Division of application No. 14/238,798, filed as application No. PCT/KR2012/006478 on Aug. 14, 2012, now abandoned.

(30) Foreign Application Priority Data

Aug. 26, 2011 (KR) .................. 10-2011-0081147
Aug. 14, 2012 (KR) .................. 10-2012-0088778

(51) Int. Cl.
| | |
|---|---|
| A61K 35/12 | (2015.01) |
| A61K 35/51 | (2015.01) |
| A61K 35/28 | (2015.01) |
| A61K 38/17 | (2006.01) |
| C12N 5/0797 | (2010.01) |
| C12N 5/071 | (2010.01) |

(52) U.S. Cl.
CPC .............. *A61K 35/28* (2013.01); *A61K 35/12* (2013.01); *A61K 35/51* (2013.01); *A61K 38/179* (2013.01); *A61K 38/1793* (2013.01); *C12N 5/069* (2013.01); *C12N 5/0623* (2013.01); *C12N 2502/11* (2013.01); *C12N 2502/1358* (2013.01)

(58) Field of Classification Search
CPC combination set(s) only.
See application file for complete search history.

(56) References Cited

FOREIGN PATENT DOCUMENTS

| | | | | |
|---|---|---|---|---|
| KR | 10-2009-0043559 | 5/2009 | | |
| KR | 10-2010-0122087 | 11/2010 | | |
| KR | 1020107019584 | * 11/2010 | ........... | C12N 5/0775 |
| KR | 10-2011-0002443 | 1/2011 | | |
| WO | 2009/050742 | 4/2009 | | |
| WO | 2009/057165 | 5/2009 | | |
| WO | 2010/070141 | 6/2010 | | |

OTHER PUBLICATIONS

Kim et al., PLoS ONE, 7(5): e37036, published May 15, 2012.*

International Search Report for PCT/KR2012/006478, dated Mar. 4, 2013.
Ratajczak, et al, "Membrane-derived microvesicles: important and underappreciated mediators of cell-to-cell communication," Leukemia (2006) 20:1487-1495.
Ratajczak, et al, "Stem Cells for Neural Regeneration—A Potential Application of Very Small Embryonic-Like Stem Cells," Journal of Physiology and Pharmacology (2011) 62:3-12.
Collino, et al. "Microvesicles Derived from Adult Human Bone Marrow and Tissue Specific Mesenchymal Stem Cells Shuttle Selected Pattern of miRNAs," PlosOne (2010), 5:e11803.
Lai, et al., "Exosome secreted by MSC reduces myocardial ischemia/reperfusion injury," Stem Cell Research (2010) 4:214-222.
Camussi, et al., "Exosomes/microvesicles as a mechanism of cell-to-cell communication," International Society of Nephrology (2010) 78:838-848.
Bruno, et al., "Mesenchymal Stem Cell-Derived Microvesicles Protect Against Acute Tubular Injury," J Am Soc Nephrol (2009) 20: 1053-1067.
Gatti, et al. "Microvesicles derived from human adult mesenchymal stem cells protect against ischaemia—reperfusion-induced acute andchronic kidney injury," Nephrol Dial Transplant (2011), 1-10.
Lai, et al. "Mesenchymal stem cell exosome: a novel stem cell-based therapy for cardiovascular disease," Regen. Med. (2011) 6:481-492.
Camussi, et al., "Exosome/microvesicle-mediated epigenetic reprogramming of cells," Am J Cancer Res (2011) 1:98-110.
Valadi, et al., "Exosome-mediated transfer of mRNAs and microRNAs is a novel mechanism of genetic exchange between cells," Nature Cell Biology (2007) 9:654.
Lee, et al. "Microvesicles as mediators of intercellular communication in cancer—the emerging science of cellular debris," Semin Immunopathol (2011), published online.
Deregibus, et al. "Endothelial progenitor cell-derived microvesicles activate an angiogenic program in endothelial cells by a horizontal transfer of mRNA," BLOOD (2007) 110(7): 2440-2448.
Choi, et al., "Enhancing trophic support of mesenchymal stem cells by ex vivo treatment with trophic factors," Journal of the Neurological Sciences (2010) 298: 28-34.
Tang, et al., "Microparticles mediate enzyme transfer from platelets to mast cells: A new pathway for lipoxin A4 biosynthesis," BBRC (2010) 400:432-436.
Chen & Zhang, "Similarity-based methods for protential human microRNA-disease associate prediction" BMC medical Genomics 2013,6:12, pp. 1-9.
Clark, et al., "Concise Review: MicroRNA Function in Multipotent Mesenchymal Stromal Cells" Stem Cells 2014, 32:1074-1082.
Bruno, et al., "Mesenchymal Stem Cell-Derived Microvesicles Protect Against Acute Tubular Injury" J. Am. Soc. Nephrol, 20:1053-1067 (2009).
Kim, et al., "Circulating Mesenchymal Stem Cells Microparticles in Patients with Cerebrovascular Disease" PLoS ONE 7(5):337036, Jan. 20, 2012.

* cited by examiner

*Primary Examiner* — Kimberly Ballard
*Assistant Examiner* — Stacey N MacFarlane
(74) *Attorney, Agent, or Firm* — McDonnell Boehnen Hulbert & Berghoff LLP

(57) ABSTRACT

The present invention relates to a composition including stem cell-derived microvesicles as an active ingredient for promoting neurogenesis. The stem cell-derived microvesicles according to the present invention can promote neurogenesis and migration of nerves and also promote angiogenesis in vascular endothelial cells, and thus can be usefully used in treatment of neurological damage.

4 Claims, 8 Drawing Sheets

Figure 1

(A) Small infarct (B) Large infarct (C)

Neural Stem Cell culture system (A)  Ctrl MSC (B)  IPC MSC

COMPOSITION INCLUDING STEM CELL-DERIVED MICROVESICLES FOR PROMOTING NEUROGENESIS

This application is a divisional of U.S. patent application Ser. No. 14/238,798 filed on Apr. 15, 2014, which is a national stage application under 35 U.S.C. § 371 of International Application No. PCT/KR2012/006478, filed Aug. 14, 2012, which claims the benefit of Korean Patent Application No. 10-2011-0081147 filed Aug. 26, 2011 and Korean Patent Application No. 10-2012-0088778 filed Aug. 14, 2012, the disclosures of which are explicitly incorporated by reference herein.

TECHNICAL FIELD

The present invention relates to a composition comprising stem cell-derived microvesicles for promoting neurogenesis and a method for promoting neurogenesis.

BACKGROUND ART

Recently, various preclinical and clinical studies on stem cell therapies have been conducted for various diseases such as cerebral infarction, traumatic neuronal injury, musculoskeletal disease, etc. However, the current technology has reached up to the level of simple extraction, culture and proliferation of stem cells and injection of the stem cells. Moreover, it is known, as a result of clinical studies up to now, that stem cell therapies have not yet shown a significant effect. Extensive research on a variety of genetically modified stem cells to promote the effect has continued to progress, but cell therapies using genes cannot be applied to the human body due to ethical issues.

Moreover, there are several problems in clinical application of the use of stem cells. Firstly, in the case of cell therapy products, there is a risk of tumor formation after stem cells are transplanted into tissue. Secondly, stem cells may cause arterial occlusion due to a relatively large size, resulting in cerebral infarction. Thirdly, stem cells can migrate to the brain during the acute phase when the brain-blood barrier is open but have limitations in crossing the brain-blood barrier due to a large size during the chronic stage. Lastly, inducing stem cells to specialized cells having desired properties for cell therapy products has limitation.

Contrarily, cell therapy using microvesicles has recently attracted attention as a method that is differentiated from the cell therapy using stem cells. Typically, microvesicles are small vesicles of 0.1 to 1 μm diameter and refer to cell membrane microparticles circulating in the blood, such as endothelial cells, platelets, etc. It is known that stem cell-derived microvesicles contain proteins, receptors as well as nuclear components and thus have a role in cell-to-cell communication. Moreover, the microvesicles contain a relatively small amount of animal serum compared to stem cells, and the risk of zoonosis can also be eliminated. In view of these characteristics of microvesicles, the cell therapy using microvesicles is expected to be a new paradigm that can overcome the limitations of existing stem cell therapies.

Therefore, extensive research aimed at using these stem cell-derived microvesicles instead of stem cells has continued to progress. For example, International Patent Publication No. WO 2010/070141 discloses a method for producing stem cell-derived microvesicles and therapeutic effects of the produced microvesicles on immune disease, allergic response, inflammatory disease, etc., and Korean Patent Publication No. 2010-122087 discloses a particle secreted by a mesenchymal stem cell and comprising at least one biological property of a mesenchymal stem cell and a technology using the particle as a therapeutic agent for cardioprotection.

However, there is not much research on stem cell-derived microvesicles, and it cannot be said that all stem cells that can be used for treatment of various diseases can be replaced by microvesicles. In particular, the correlation between microvesicles and neurogenesis has not been reported.

Therefore, if the generation of neuronal cells can be promoted using stem cell-derived microvesicles, it is possible to use them in the treatment of diseases related to neurological damage, and thus there is an urgent need to study the correlation between microvesicles and neuronal cells.

DISCLOSURE

Technical Problem

The present inventors have studied the correlation between microvesicles and neuronal cells and found that stem cell-derived microvesicles have excellent effects of promoting neurogenesis and migration of neuronal cells and promoting angiogenesis in vascular endothelial cells, thus completing the present invention.

Technical Solution

To achieve the above objects, the present invention provides a composition for promoting neurogenesis, comprising stem cell-derived microvesicles as an active ingredient.

Moreover, the present invention provides a method for promoting neurogenesis, comprising the step of applying stem cell-derived microvesicles to neural stem cells.

Furthermore, the present invention provides a pharmaceutical composition for prevention or treatment of degenerative neurological diseases, comprising stem cell-derived microvesicles as an active ingredient.

In addition, the present invention provides a method for treating neurological damage, comprising the step of treating a subject other than human, suffering from neurological damage, with stem cell-derived microvesicles.

Advantageous Effects

The stem cell-derived microvesicles according to the present invention have excellent effects of promoting neurogenesis and migration of neuronal cells and promoting angiogenesis of vascular endothelial cells, thus treating neurological damage.

MODE FOR INVENTION

The present invention provides a composition for promoting neurogenesis, comprising stem cell-derived microvesicles as an active ingredient.

Moreover, the present invention provides a method for promoting neurogenesis, comprising the step of applying stem cell-derived microvesicles to neural stem cells.

As used herein, the term "stem cell-derived microvesicles" refers to small vesicles derived from stem cells, containing receptors and proteins, and having a diameter of 0.1 to 1 μm.

The stem cell-derived microvesicles may be microvesicles derived from stem cells induced by ischemic stimuli, and the ischemic stimuli may preferably be ischemic preconditioning stimuli. The ischemic preconditioning stimuli may be performed by exposing stem cells to an environment that causes ischemia or treating stem cells with ischemic brain extract.

The ischemic brain extract may be an extract obtained from the brain of subjects that have ischemic symptoms. The one example of ischemic symptoms may be ischemic stroke.

The stem cell-derived microvesicles may include, but not particularly limited to, CD105 positive microvesicles, annexin V-negative microvesicles, etc. which are specific to mesenchymal stem cells Here, the stem cells that are the source of the microvesicles may be, but not limited to, any one of induced pluripotent stem cells (iPS), adult stem cells, embryonic stem cells, mesenchymal stem cells, adipose stem cells, hematopoietic stem cells, and cord blood stem cells, preferably mesenchymal stem cells.

The stem cell-derived microvesicles according to the present invention can promote neurogenesis and migration of neuronal cells and also promote angiogenesis in vascular endothelial cells.

Moreover, the present invention provides a pharmaceutical composition for prevention or treatment of degenerative neurological diseases, comprising stem cell-derived microvesicles as an active ingredient.

The stem cell-derived microvesicles according to the present invention can promote neurogenesis and migration of neuronal cells and promote angiogenesis in vascular endothelial cells, thus having excellent effect of treating neurological damage. Therefore, the stem cell-derived microvesicles according to the present invention can be effectively used in prevention or treatment of degenerative neurological diseases.

As used herein, the term "degenerative neurological diseases" is intended to include, but not limited to, a variety of diseases caused by neurological damage without limitation, and an example of the degenerative neurological diseases may be any one of ischemic stroke, cerebral infarction, neurotrauma, Parkinson's disease, Lou Gehrig' disease, and epilepsy.

The pharmaceutical composition for prevention or treatment of degenerative neurological diseases, comprising stem cell-derived microvesicles as an active ingredient according to the present invention may preferably contain other ingredients which may provide a synergy effect to the main effect within a range of not impairing the main effect of the present invention, in addition to the stem cell-derived microvesicles.

Moreover, the pharmaceutical composition of the present invention may further comprise pharmaceutically acceptable carrier, excipients, and diluents for administration, in addition to the above-described active ingredient. Examples of carriers, excipients, and diluents may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, and mineral oil.

The pharmaceutical composition of the present invention may be formulated into various formulations for parenteral or oral administration. A representative example of the parenteral formulation may preferably be an isotonic aqueous solution or as an injectable formulation. The injectable formulation may be prepared by a method known in the art using a suitable dispersant or wetting agent and a suspending agent by any method known in the art. For example, the respective ingredients may be dissolved in a saline or buffer solution to be formulated into an injectable formulation.

Solid formulations for oral administration may include tablets, pills, powders, granules, capsules, etc. The solid formulations may be prepared by mixing the active ingredient with at least one excipient such as starch, calcium carbonate, sucrose, lactose, gelatin, etc. Moreover, lubricants such as magnesium stearate, talc, etc. may be used in addition to simple excipients.

Liquid formulations for oral administration may include suspensions, internal solutions, emulsions, syrups, etc. The liquid formulations may include, and various excipients such as humectants, sweeteners, aromatics, preservatives, etc. may be included in addition to generally-used simple diluents such as water and liquid paraffin.

Formulations for parenteral administration may include sterile solutions, non-aqueous solvents, suspensions, emulsions, freeze-dried formulations, and suppositories. Propylene glycol, polyethylene glycol, vegetable oil such as olive oil, and injectable ester such as ethyl oleate, etc. may be used for non-aqueous solvents and suspensions. Witepsol, macrogol, Tween 61, cacao oil, laurin oil, glycerogelatin, etc. may be used for suppository bases.

The effective dosage of the pharmaceutical composition of the present invention may vary depending on the age, gender, and weight of a patient. However, the pharmaceutical composition of the present invention may be administered in a dose of 100 μg/kg to 1 mg/kg, preferably 200 μg/kg to 500 μg/kg.

For the prevention or treatment of degenerative neurological diseases, the composition of the present invention may be used alone or in combination with surgical operation, chemical therapy, radiotherapy, hormonal therapy, chemical therapy, drug therapy, and methods using biological response modifiers.

Moreover, the present invention provides a method for treating neurological damage, comprising the step of treating a subject other than human, suffering from neurological damage, with stem cell-derived microvesicles.

The treatment with stem cell-derived microvesicles promotes neurogenesis and migration of neuronal cells and also promotes angiogenesis in vascular endothelial cells, thus effectively treating neurological damage.

As used here, the term "neurological damage" refers to damage to the nerve caused by physical factors or degenerative neurological diseases. The neurological damage by physical factors may include, but not limited to, brain trauma, spinal cord injury, cerebral infarction, cerebral hemorrhage, neurotrauma, etc., and the neurological damage by degenerative neurological disease may include, but not limited to, ischemic stroke, cerebral infarction, neurotrauma, Parkinson's disease, Lou Gehrig' disease, and epilepsy.

The subject other than human may preferably include, but not limited to, a rat, a red fox, a skunk, a raccoon, a badger, a dog, a wolf, a mongoose, a coyote, a weasel, and a cat.

MODE FOR INVENTION

In the following, the present invention will be described in detail with reference Preparation Examples and Examples. However, the following Preparation Examples and Examples are provided only for illustration of the present invention, and the present invention is not limited by the following Preparation Examples and Examples.

Example 1: Comparison of the Levels of Stem Cell-Derived Microvesicles in Serum

Citrated sera were collected from stroke patients and centrifuged at 19,800 g and 10° C. for 10 minutes to obtain stem cell-derived microvesicles. The obtained stem cell-derived microvesicles were suspended in 20 μl PBS, and the blood levels of stem cell-derived microvesicles (CD105-positive/annexin V-negative) and microvesicles (CXCR4-positive/annexin V-negative) expressing the SDF-1 receptor, CXCR4, were compared in patients with a small infarct (DWI volume: 10 cc or less) and patients with a large infarct (DWI volume: 10 cc or more), and it was determined whether CD105-positive cells were CD90-positive or double-positive cells. The results of the above experiment are shown in FIG. 1.

Figure 1:
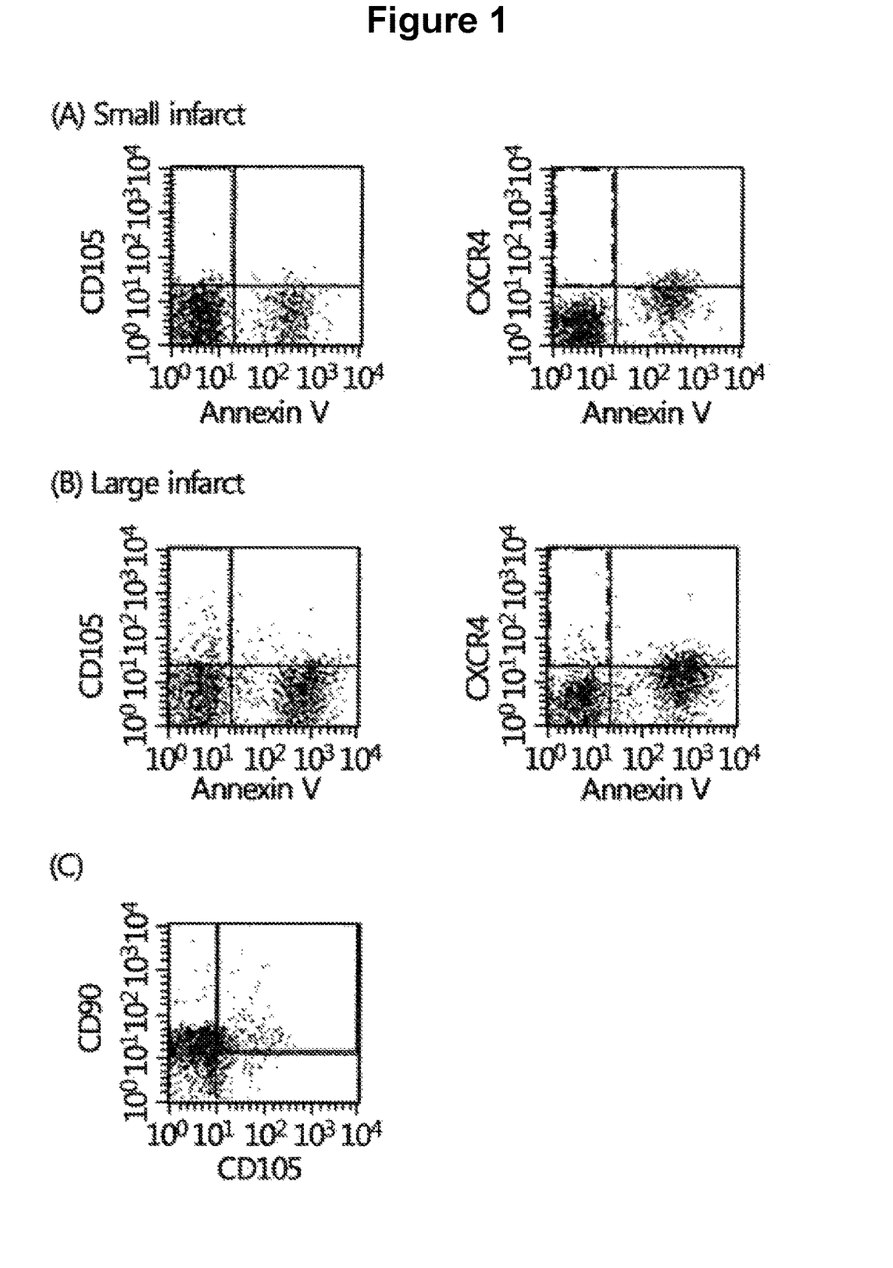
FIG. 1 shows blood levels of CD105-positive/annexin V-negative and CXCR4-positive/annexin V-negative microvesicles in a patient with a small infarct (A) and in a patient with a large infarct (B) and the correlation between CD105-positive and CD90-positive (C).

As shown in FIG. 1, it was found that the amount of CD105-positive cells and CXCR4-positive cells in patients with a large infarct (B) after the onset of cerebral infarction was greater than that in patients with a small infarct (A). It can be seen from this result that the number of stem cell-derived microvesicles and microvesicles capable of migrating by SDF-1 chemotaxis increases in patients with a large infarct. Moreover, it was found that most CD105-positive cells were CD90 double-positive cells, indicating that CD105-positive microvesicles were derived from stem cells.

Meanwhile, based on clinical records of stroke patients, the correlation between stem cell-derived microvesicles (CD105-positive/annexin V-negative), microvesicles expressing the SDF-1 receptor, CXCR4 (CXCR4-positive/annexin V-negative), and SDF-1α according to the diffusion weighted image (DWI) showing the infarct size, the National Institutes of Health Stroke Scale (NIHSS), and the time since the onset of cerebral infarction was analyzed. The results of the above experiment are shown in FIG. 2.

Figure 2:
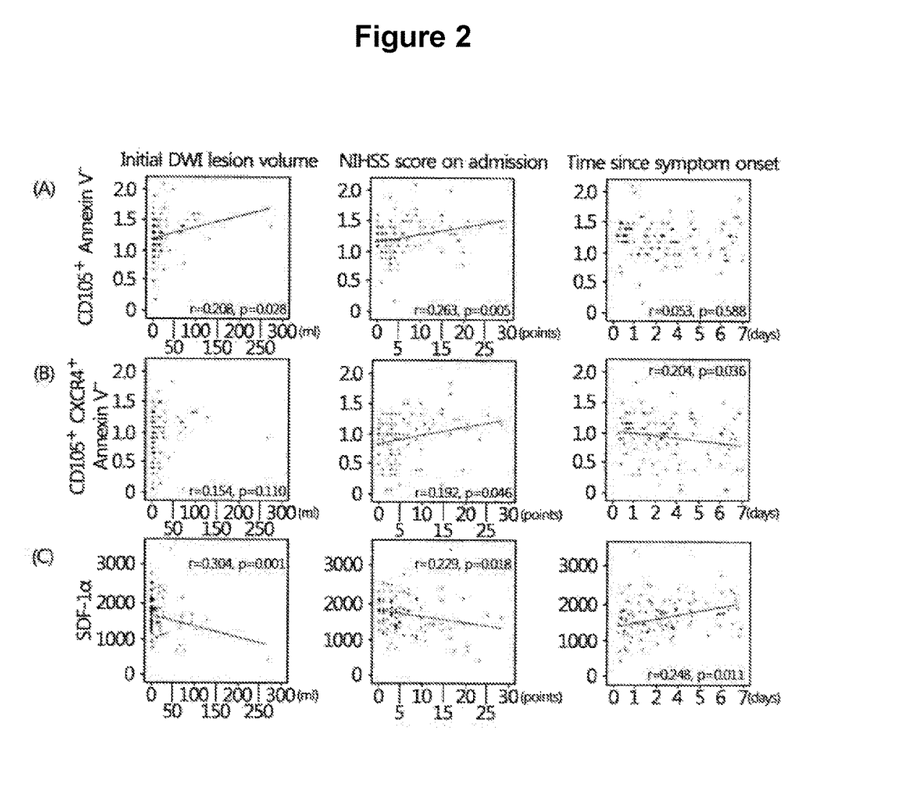
FIG. 2 shows the correlation between CD105-positive/annezin V-negative microvesicles (A), CD105-positive/CXCR4-positive/annexin V-negative microvesicles (B), and SDF-1α (C) according to the infarct size (DWI), NIHSS, and the time since the onset of cerebral infarction.

As shown in FIG. 2, the number of CD105-positive/annexin V-negative stem cell-derived microvesicles showed a tendency to increase as the infarct size was larger and the NIHSS score was higher (A), and the number of CD105-positive/CXCR4-positive/annexin V-negative microvesicles showed a tendency to increase as the NIHSS score was higher and to decrease as the time since the onset of cerebral infarction increased (B). It can be seen from these results that the blood level of stem cells with high motility was increased by microvesicles as the severity of cerebral infarction was higher, indicating that the existence of potential stem cells may decrease as the time since the onset of cerebral infarction increases. Meanwhile, the blood concentration of SDF-1α decreased as the infarct size was larger and increased as the time since the onset of cerebral infarction increased (C).

Example 2: Isolation of Microvesicles from Bone Marrow-Derived Stem Cells 2.1 Collection and Culture of Mesenchymal Stem Cells Bone marrows were collected from the femur of rats to obtain bone marrow-derived mesenchymal stem cells by culture. The obtained mesenchymal stem cells were cultured at a density of $1 \times 10^5$ cell/ml in T75 flask at 5% $CO_2$ and 37° C. and subcultured at 80% confluence. The subculture was performed in a manner that the medium was removed, the stem cells were gently washed with PBS more than once, cultured in a 37° C. incubator for about 1 minute after addition of Tryple (Invitrogen), and placed in a medium containing 10% FBS fetal bovine serum (FBS) to neutralize the reaction, and then the cells were collected and centrifuged at 1,300 g for 4 minutes. The cell precipitates were resuspended in a medium containing FBS, counted, and cultured. The fourth to sixth passage cells were used in the experiment. Low-glucose DMEM containing 10% FBS and 1% penicillin/streptomycin was used as a medium.

2.2 Preparation of Simulatives for Ischemic Preconditioning Stimuli

Hemispheric tissues of white rats with induced middle cerebral artery occlusion were fragmented in 150 mg/ml DMEM medium and then centrifuged at 10,000 g for 10 minutes, and the supernatant was collected to obtain ischemic brain extracts. The obtained ischemic brain extracts were plated in equal amounts and kept at −70° C. For application of ischemic stimuli to stem cells, the stem cells were suspended in DMEM medium to prepare 20% ischemic brain extract, thus preparing stimulatives for ischemic preconditioning stimuli containing 20% ischemic brain extract or 20% ischemic serum.

2.3 Isolation and Analysis of Stem Cell-Derived Microvesicles

Figure 3:
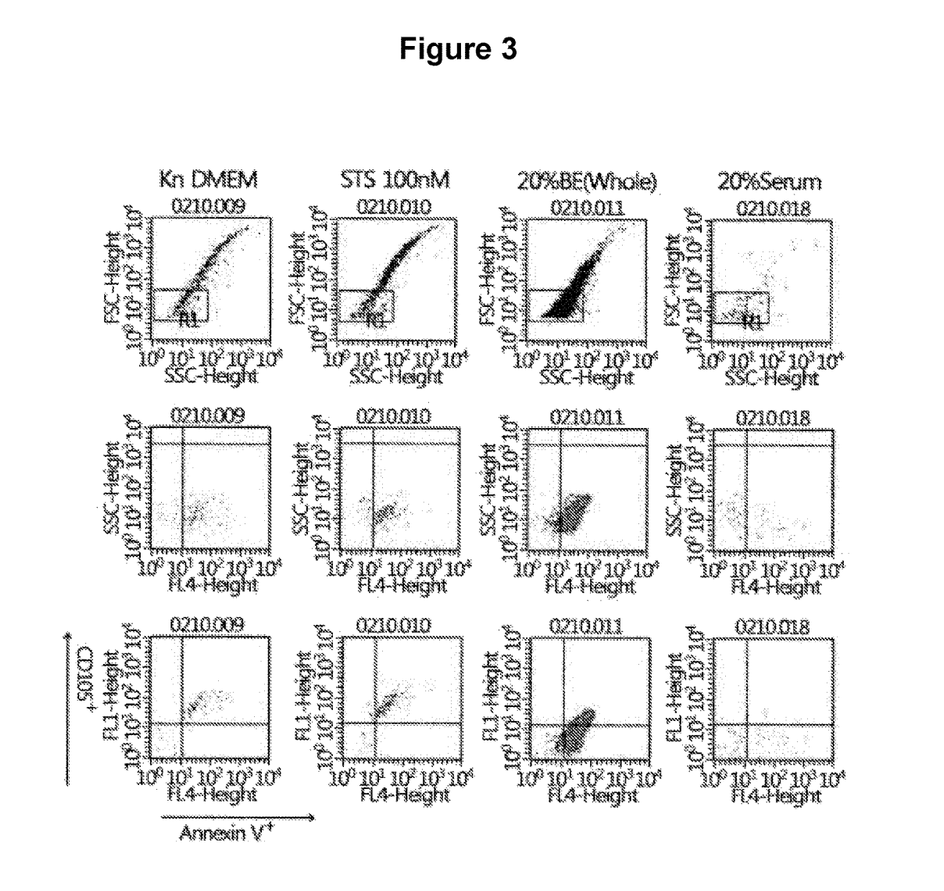
FIG. 3 shows the numbers of stem cell-derived microvesicles in bone marrow-derived mesenchymal stem cells treated with Kn DEME (knockout DEME), STS 100 nm (staurosporin A), 20% ischemic brain extract (20% BE (whole)), and 20% ischemic serum (20% serum), determined by a flow cytometer using CD105 and annexin V.

The bone marrow-derived mesenchymal stem cells prepared in Example 2.1 were cultured in a 60 mm culture dish in DMEM medium containing 10% FBS. The stimulatives for ischemic preconditioning stimuli (20% ischemic brain extract or 20% ischemic serum) prepared in Example 2.2 were added, and then the supernatant was collected from the culture medium. The supernatant was centrifuged at low speed (2,500 g, 10° C., 10 minutes) to remove impurities from the supernatant and centrifuged again at high speed (14,500 g, 10° C., 45 minutes), thus obtaining microvesicles derived from stem cells. The number of the obtained microvesicles was calculated by the following formula, and the expression degree of CD105 and annexin V in each microvesicle was analyzed using a flow cytometer.

The number of microvesicles (n/L)=(the total amount of microvesicle suspension/the amount of microvesicles used in the antibody response)×(the total amount of microvesicle diluent for flow cytometry/the amount of microvesicle diluent used for flow cytometry)× ($10^6$/the total amount of serum)

The expression degree of CD105 and annexin V was used as a marker to determine whether the microvesicles were derived from mesenchymal stem cells, and microvesicles obtained from bone marrow-derived mesenchymal stem cells treated with knockout DEME and staurosporin A were used as controls. The results of the above experiment are shown in FIG. 3.

As shown in FIG. 3, it can be seen that the amount of microvesicles obtained from bone marrow-derived mesenchymal stem cells did not increase in the control groups treated with Kn DEME (knockout DEME), STS 100 nm (staurosporin A), and 20% ischemic serum (20% serum), but the amount of microvesicles significantly increased in the group treated with 20% ischemic brain extract (20% BE (whole)). Therefore, it was found that it was desirable to use the ischemic brain extract in order to increase the secretion of microvesicles.

2.4 Determination of Safety of Stem Cell-Derived Microvesicles

It was determined whether cell death was induced when neuronal cells under culture were treated with microvesicles obtained by ischemic preconditioning. The neuronal cell death was determined by LDH analysis 24 hours after treating neuronal cell culture with microvesicles (1, 3, 10, 30 μg/ml) obtained by ischemic preconditioning or with 30 μm NMDA (positive control). The results of the above experiment are shown in FIG. 4.

Figure 4:
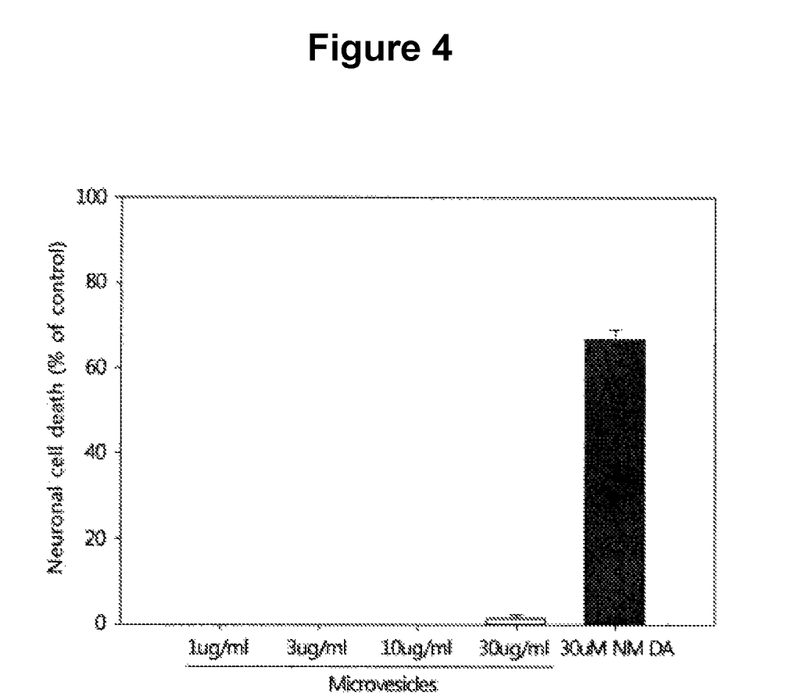
FIG. 4 shows neuronal cell deaths after treatment of neuronal cells with stem cell-derived microvesicles (1, 3, 10, 30 μg/ml) obtained by ischemic stimuli or with 30 μm NMDA as a control, determined by LDH analysis.

As shown in FIG. 4, it was found that microvesicles obtained by ischemic preconditioning did not cause neuronal cell death, but more than 70% neuronal cell death occurred in the group treated with NMDA. Therefore, it can be seen that the microvesicles obtained by ischemic preconditioning do not induce the death of neural stem cells and thus is considered as a safe material.

Example 3: Stimulation of Neural Stem Cells Using Stem Cell-Derived Microvesicles 3.1 Isolation and Culture of Neural Stem Cells Brain tissues collected from 14-day-old embryonic rats were gently fragmented using a narrow-bore glass pipette or dissociated to single cell level using a cell dissociation solution such as Accutase and centrifuged (500 g, 5 minutes), thus obtaining precipitated cells. The obtained cells were cultured in DMEM/F12 medium containing 1XN2 supplement, 25 ng/ml bFGF, and 25 ng/ml EGF to induce neural stem cells. The induced neural stem cells were subcultured such that the diameter of the neuronal cell is maintained within 100 nm.

3.2 Increase in Neurogenesis Capability of Neural Stem Cells by Stem Cell-Derived Microvesicles The neural stem cells induced in Example 3.1 were treated with the stem cell-derived microvesicles obtained in Example 2.3 by ischemic preconditioning, and the neurogenesis capabilities of the treated neural stem cells were compared. Microvesicles obtained from mesenchymal stem cells without ischemic stimuli were used as a control. Each experimental group was observed under an optical microscope and a confocal microscope. Nestin as a marker for neural stem cells and doublecortin (DCX) as a marker for neural progenitor cells were used, and their differentiation into astroglial cells was determined. The results of the above experiment are shown in FIG. 5.

Figure 5:
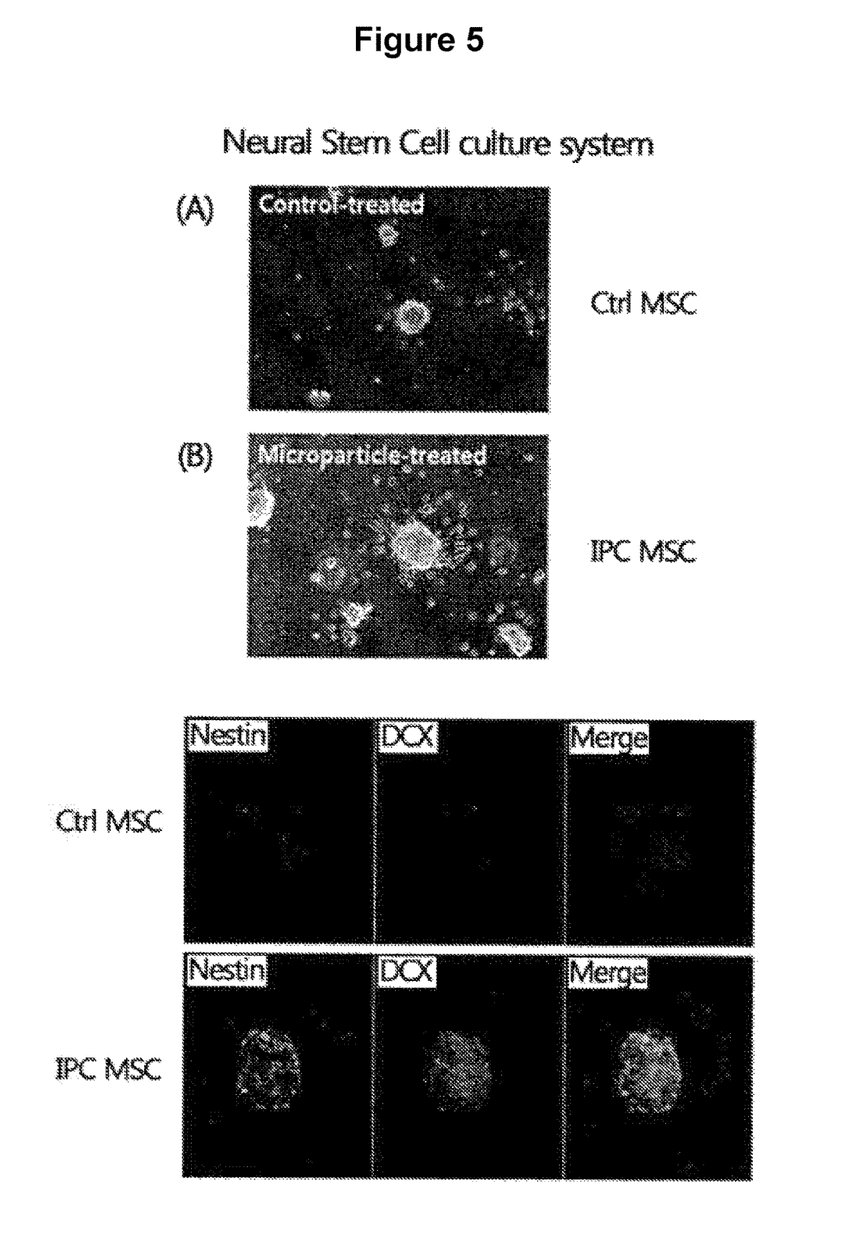
FIG. 5 shows neurogenesis capabilities after treatment of neuronal stem cells with microvesicles obtained without ischemic stimuli (A) or with stem cell-derived microvesicles obtained by ischemic stimuli (B), determined by an optical microscope and a confocal microscope.

As shown in FIG. 5, it was found that the neurogenesis capability did not significantly increase in neural stem cells treated with microvesicles obtained without ischemic stimuli (A), but the expression of nestin and DCX markers significantly increased in neural stem cells treated with microvesicles obtained by applying ischemic stimuli to bone marrow stem cells (B), representing the increase in neurogenesis capability.

3.3 Increase in Angiogenesis Capability of Vascular Endothelial Cells by Stem Cell-Derived Microvesicles Vascular endothelial cells were treated with the microvesicles (1, 3, 10, 30 μg/ml) obtained in Example 2.2 by ischemic stimuli, and the angiogenesis capabilities of vascular endothelial cells were compared. Microvesicles obtained from mesenchymal stem cells without ischemic stimuli were used as a control. Living cells were fluorescence-stained with Calcein AM to be used as a marker to measure the angiogenesis capability and observed under a fluorescence microscope. The results of the above experiment are shown in FIG. 6.

Figure 6:
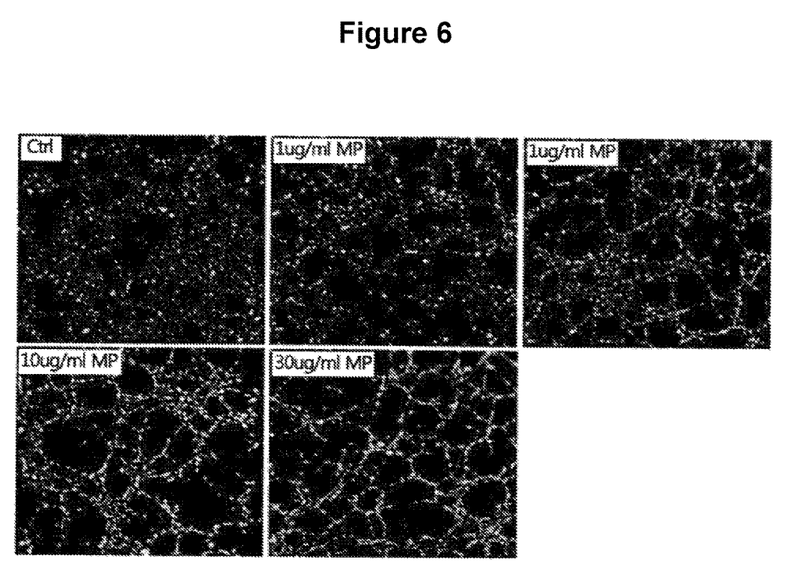
FIG. 6 shows angiogenesis capabilities of vascular endothelial cells after treatment with microvesicles (1, 3, 10, 30 μg/ml) obtained by ischemic stimuli, determined by a fluorescence microscope.

As shown in FIG. 6, it was found that the increase in fluorescence was not observed in the control group (ctrl), but the fluorescence increased in a concentration-dependent manner by angiogenesis in vascular endothelial cells after treatment with stem cell-derived microvesicles. Therefore, it can be seen that the stem cell-derived microvesicles can promote angiogenesis in vascular endothelial cells.

3.4 Stimulation of Neural Stem Cells by Stem Cell-Derived Microvesicles in Ischemic Stroke Animals (In Vivo)

Figure 7:
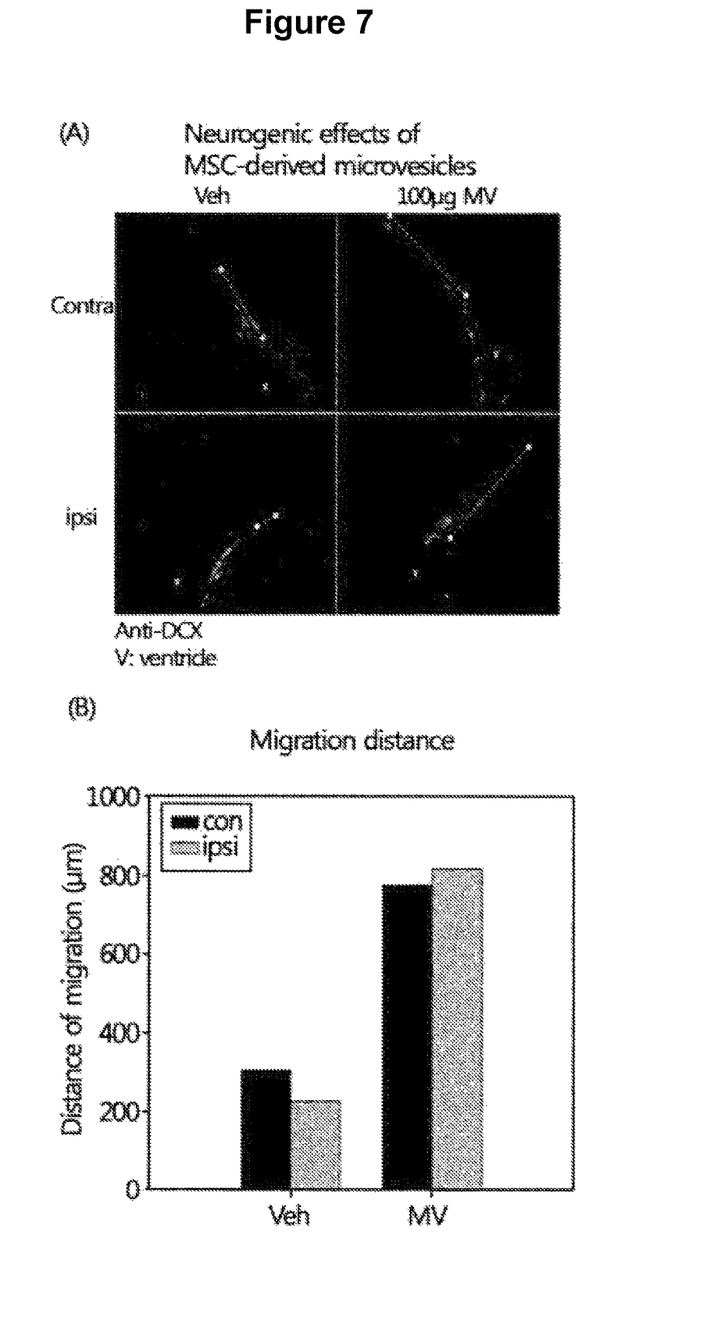
FIG. 7 shows migration distances of neural progenitor cells after injection of microvesicles obtained by ischemic stimuli into the ventricle of rats with ischemic stroke, determined by fluorescence staining (A) and shows the numerical results thereof (B) (Contra: contralateral, ipsi: ipsilateral).

The microvesicles obtained in Example 2.3 by ischemic stimuli were injected into the ventricle of rats with ischemic stroke, and the migration distances of neural progenitor cells were compared. PBS containing no microvesicles was injected into the ventricle and used as a control, and the microvesicles were fluorescence-stained with antibodies against the DCX marker for neural progenitor cells.

The results are shown in FIG. 7.

As shown in FIG. 7, it was found that the injection of stem cell-derived microvesicles into the ventricle of rats with ischemic stroke significantly increased the migration distance of neural progenitor cells in both the ipsilateral (ipsi) and contralateral (contra) of the ventricle, compared to the control group (Veh) treated PBS. Therefore, it can be seen that the stem cell-derived microvesicles can stimulate neural progenitor cells to promote their migration.

3.5 Promotion of Neurogenesis by Stem Cell-Derived Microvesicles in Ischemic Stroke Animals (In Vivo)

The microvesicles obtained in Example 2.3 by ischemic stimuli were injected into the ventricle of rats with ischemic stroke, and the degrees of angiogenesis of vascular endothelial cells were compared. PBS containing no microvesicles was injected into the ventricle and used as a control, and the microvesicles were fluorescence-stained with antibodies against Von Willebrand factor (vWF), a marker for neural progenitor cells. The results of the above experiment are shown in FIG. 8.

Figure 8:
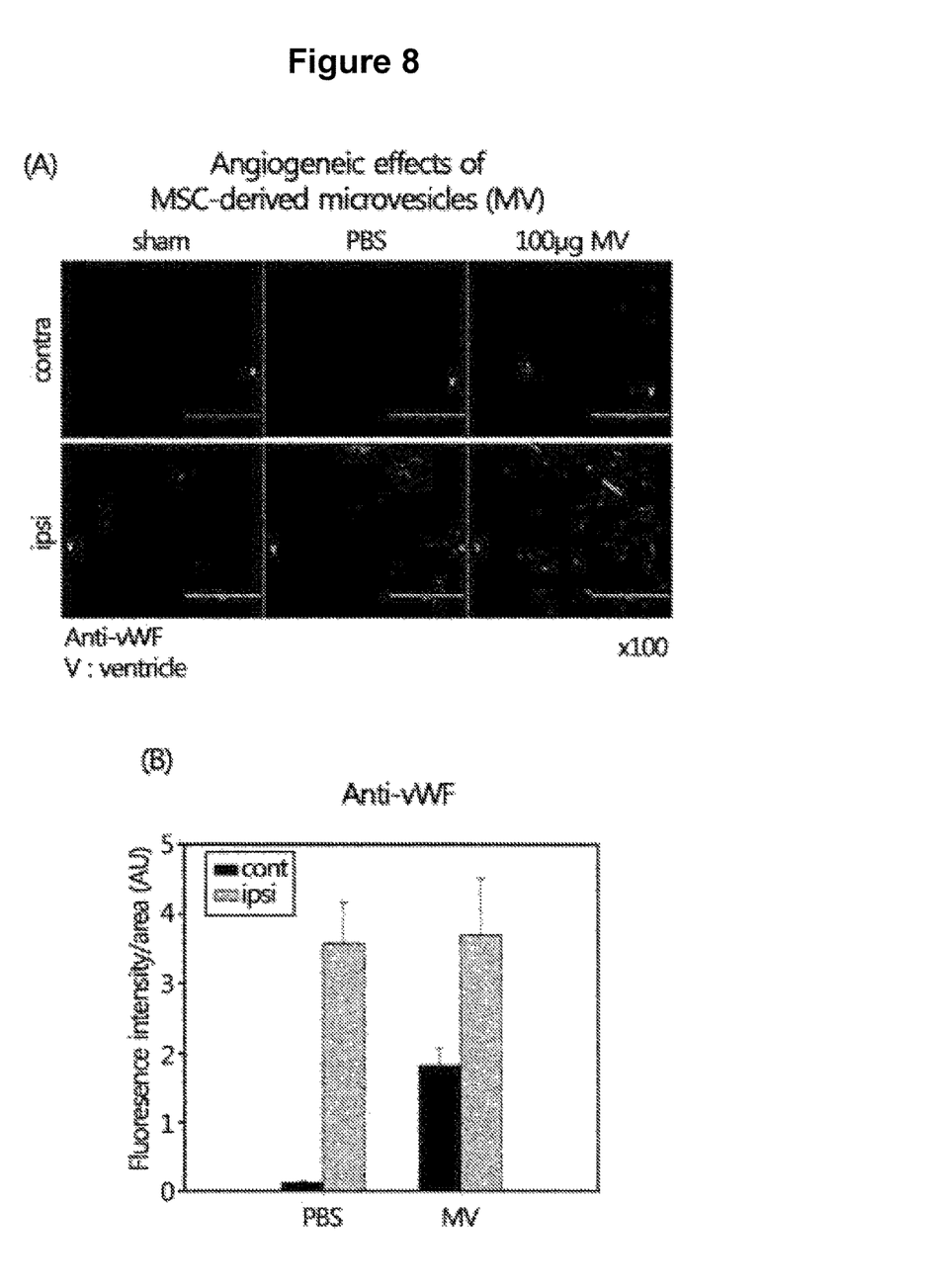
FIG. 8 shows angiogenesis of vascular endothelial cells after injection of stem cell-derived microvesicles obtained by ischemic stimuli into the ventricle of rats with ischemic stroke, determined by fluorescence staining (A) and shows the numerical results thereof (B) (Contra: contralateral, ipsi: ipsilateral, sham: normal control group).

As shown in FIG. 8, it was found that the neurogenesis increased in both the ipsilateral (ipsi) and contralateral (contra) of the ventricle and, in particular, significantly increased in the contralateral of the ventricle in the experimental group treated with stem cell-derived microvesicles, compared with the normal control and the PBS-treated control group (sham). Therefore, it can be seen that the stem cell-derived microvesicles can promote the migration of neural progenitor cells and also promote angiogenesis in vascular endothelial cells.

The invention claimed is:

1. A method for promoting neurogenesis, comprising the steps of:
    (a) treating mesenchymal stem cells in vitro with an ischemic tissue extract;
    (b) obtaining microvesicles from the mesenchymal stem cells of step (a); and
    (c) treating neural stem cells in vitro with the microvesicles of step (b) as an active ingredient.

2. The method for promoting neurogenesis of claim 1, wherein the ischemic tissue extract is an ischemic brain extract.

3. The method for promoting neurogenesis of claim 1, wherein the microvesicles are CD105-positive and annexin V-negative microvesicles identified by flow cytometry.

4. A method for treating ischemic stroke or cerebral infarction, comprising the steps of;
    (a) treating mesenchymal stem cells in vitro with an ischemic tissue extract;
    (b) obtaining microvesicles from the mesenchymal stem cells of step (a); and
    (c) administering the microvesicles of step (b) as an active ingredient to a subject with ischemic stroke of cerebral infarction.

* * * * *